(12) United States Patent
Tatalovich et al.

(10) Patent No.: US 11,083,608 B2
(45) Date of Patent: *Aug. 10, 2021

(54) STENT RETAINING SYSTEMS

(71) Applicant: Covidien LP, Mansfield, MA (US)

(72) Inventors: Joe Tatalovich, St. Louis Park, MN (US); Sara Thorson, Ann Arbor, MI (US); Megan Miezwa, Maple Grove, MN (US); Steven G. Zaver, Plymouth, MN (US); Richard S. Kusleika, Excelsior, MN (US); Paul Noffke, St. Paul, MN (US)

(73) Assignee: Covidien LP, Mansfield, MA (US)

( * ) Notice: Subject to any disclaimer, the term of this patent is extended or adjusted under 35 U.S.C. 154(b) by 489 days.

This patent is subject to a terminal disclaimer.

(21) Appl. No.: 15/994,322

(22) Filed: May 31, 2018

(65) Prior Publication Data
US 2018/0325709 A1 Nov. 15, 2018

Related U.S. Application Data

(63) Continuation of application No. 13/364,772, filed on Feb. 2, 2012, now Pat. No. 10,028,854.

(51) Int. Cl.
*A61F 2/962* (2013.01)
*A61F 2/915* (2013.01)
(Continued)

(52) U.S. Cl.
CPC .............. *A61F 2/962* (2013.01); *A61F 2/915* (2013.01); *A61F 2/9517* (2020.05);
(Continued)

(58) Field of Classification Search
CPC ...... A61F 2002/9505; A61F 2002/9511; A61F 2002/9665; A61F 2/915; A61F 2/9517; A61F 2/962
See application file for complete search history.

(56) References Cited

U.S. PATENT DOCUMENTS

| 5,261,916 A | 11/1993 | Engelson |
| 5,403,341 A | 4/1995 | Solar |

(Continued)

FOREIGN PATENT DOCUMENTS

| CA | 2371759 A1 | 11/2000 |
| CN | 2933337 Y | 8/2007 |

(Continued)

OTHER PUBLICATIONS

Australian Search Report dated Jul. 18, 213 from corresponding AU Application No. 2013200097 (4 pgs.).

(Continued)

*Primary Examiner* — Julie A Szpira
(74) *Attorney, Agent, or Firm* — Shumaker & Sieffert, P.A.

(57) ABSTRACT

A stent delivery system includes an expandable stent, a catheter, and a sheath. The expandable stent includes proximal and distal ends, and a first interlock structure. The catheter includes an elongated member having a second interlock structure displaceably arranged about an outer surface thereof for engaging the first interlock structure of the stent. The sheath is mounted on the elongated member and is positionable in a transport position in which the sheath covers the stent mounted on the elongated member and a deploy position in which the stent is exposed.

20 Claims, 14 Drawing Sheets

(51) Int. Cl.
*A61F 2/95* (2013.01)
*A61F 2/966* (2013.01)

(52) U.S. Cl.
CPC ............. *A61F 2002/9505* (2013.01); *A61F 2002/9511* (2013.01); *A61F 2002/9665* (2013.01)

(56) References Cited

U.S. PATENT DOCUMENTS

| | | |
|---|---|---|
| 5,554,181 A | 9/1996 | Das |
| 5,690,644 A | 11/1997 | Yurek et al. |
| 5,702,418 A | 12/1997 | Ravenscroft |
| 5,709,703 A | 1/1998 | Lukic et al. |
| 5,733,325 A | 3/1998 | Robinson et al. |
| 5,776,141 A | 7/1998 | Klein et al. |
| 5,944,726 A | 8/1999 | Blaeser et al. |
| 5,989,280 A | 11/1999 | Euteneuer et al. |
| 6,077,295 A | 6/2000 | Limon et al. |
| 6,077,297 A | 6/2000 | Robinson et al. |
| 6,102,942 A | 8/2000 | Ahari |
| 6,120,522 A | 9/2000 | Vrba et al. |
| 6,132,461 A | 10/2000 | Thompson |
| 6,251,132 B1 | 6/2001 | Ravenscroft et al. |
| 6,267,783 B1 | 7/2001 | Letendre et al. |
| 6,315,790 B1 | 11/2001 | Gerberding et al. |
| 6,350,278 B1 | 2/2002 | Lenker et al. |
| 6,428,566 B1 | 8/2002 | Holt |
| 6,468,298 B1 | 10/2002 | Pelton |
| 6,558,415 B2 | 5/2003 | Thompson |
| 6,562,063 B1 | 5/2003 | Euteneuer et al. |
| 6,607,551 B1 | 8/2003 | Sullivan et al. |
| 6,623,491 B2 | 9/2003 | Thompson |
| 6,623,518 B2 | 9/2003 | Thompson et al. |
| 6,629,992 B2 | 10/2003 | Bigus et al. |
| 6,656,212 B2 | 12/2003 | Ravenscroft et al. |
| 6,682,553 B1 | 1/2004 | Webler, Jr. |
| 6,685,735 B1 | 2/2004 | Ahari |
| 6,755,855 B2 | 6/2004 | Yurek et al. |
| 6,776,791 B1 | 8/2004 | Stallings et al. |
| 6,814,746 B2 * | 11/2004 | Thompson ............... A61F 2/95 623/1.11 |
| 6,818,013 B2 | 11/2004 | Mitelberg et al. |
| 6,827,732 B2 | 12/2004 | Thompson |
| 6,858,034 B1 * | 2/2005 | Hijlkema ............... A61F 2/95 606/108 |
| 6,902,575 B2 | 6/2005 | Laakso et al. |
| 6,964,676 B1 | 11/2005 | Gerberding et al. |
| 7,022,132 B2 | 4/2006 | Kocur |
| 7,025,791 B2 | 4/2006 | Levine et al. |
| 7,172,617 B2 | 2/2007 | Colgan et al. |
| 7,235,093 B2 * | 6/2007 | Gregorich ............... A61F 2/91 623/1.11 |
| 7,264,632 B2 | 9/2007 | Wright et al. |
| 7,303,580 B2 | 12/2007 | Parker |
| 7,473,271 B2 | 1/2009 | Gunderson |
| 7,517,361 B1 | 4/2009 | Ravenscroft |
| 7,632,296 B2 | 12/2009 | Malewicz |
| 7,771,463 B2 * | 8/2010 | Ton ............... A61F 2/90 623/1.11 |
| 7,785,361 B2 | 8/2010 | Nikolchev et al. |
| 8,257,427 B2 | 9/2012 | Andersen et al. |
| 9,173,751 B2 | 11/2015 | Schmid et al. |
| 9,381,104 B2 | 7/2016 | Berez et al. |
| 10,010,418 B2 | 7/2018 | Marchand et al. |
| 10,028,854 B2 | 7/2018 | Tatalovich et al. |
| 2002/0095203 A1 | 7/2002 | Thompson et al. |
| 2002/0120322 A1 * | 8/2002 | Thompson ............... A61F 2/95 623/1.11 |
| 2003/0074043 A1 | 4/2003 | Thompson |
| 2004/0087900 A1 | 5/2004 | Thompson et al. |
| 2004/0102791 A1 | 5/2004 | Murray, III |
| 2004/0106977 A1 | 6/2004 | Sullivan et al. |
| 2005/0222662 A1 * | 10/2005 | Thompson ............... A61F 2/95 623/1.11 |
| 2006/0058866 A1 | 3/2006 | Cully et al. |
| 2006/0142838 A1 | 6/2006 | Molaei et al. |
| 2006/0276886 A1 | 12/2006 | George et al. |
| 2007/0233224 A1 | 10/2007 | Leynov et al. |
| 2007/0289677 A1 * | 12/2007 | Ma ............... A61F 2/86 148/563 |
| 2008/0015610 A1 | 1/2008 | Kaplan et al. |
| 2008/0065000 A1 * | 3/2008 | Bidinger ............... F16L 37/0885 604/9 |
| 2008/0255655 A1 * | 10/2008 | Kusleika ............... A61F 2/91 623/1.11 |
| 2009/0171434 A1 | 7/2009 | Rusk et al. |
| 2009/0177261 A1 | 7/2009 | Teoh et al. |
| 2009/0177288 A1 | 7/2009 | Wallsten |
| 2009/0187238 A1 | 7/2009 | Weber et al. |
| 2009/0254165 A1 | 10/2009 | Tabor et al. |
| 2010/0274344 A1 | 10/2010 | Dusbabek et al. |
| 2011/0077731 A1 | 3/2011 | Lee et al. |
| 2011/0137401 A1 | 6/2011 | Dorn et al. |
| 2011/0319904 A1 | 12/2011 | Hollett et al. |
| 2012/0316636 A1 * | 12/2012 | Young ............... A61F 2/95 623/1.12 |
| 2013/0073026 A1 * | 3/2013 | Russo ............... A61F 2/90 623/1.12 |

FOREIGN PATENT DOCUMENTS

| | | |
|---|---|---|
| CN | 101083957 A | 12/2007 |
| CN | 101180006 A | 5/2008 |
| CN | 101267780 A | 9/2008 |
| CN | 101553190 A | 10/2009 |
| CN | 101779993 A | 7/2010 |
| DE | 19547617 | 9/1997 |
| EP | 0335341 A1 | 10/1989 |
| EP | 1157673 A1 | 11/2001 |
| EP | 1415616 A1 | 5/2004 |
| JP | 2006522654 A | 10/2006 |
| JP | 2009513200 A | 4/2009 |
| JP | 2011147791 | 8/2011 |
| JP | 2012000327 A | 1/2012 |
| WO | 9716133 | 5/1997 |
| WO | 2002/056798 | 7/2002 |
| WO | 02067782 A2 | 9/2002 |
| WO | 2004091450 A2 | 10/2004 |
| WO | 2007147156 A1 | 12/2007 |
| WO | 2008124728 A1 | 10/2008 |

OTHER PUBLICATIONS

European Search Report dated Jun. 12, 2013 from corresponding EP Application No. EP 13150274.2 (9 pgs.).
English translation of Japanese Office Action, dated Jan. 31, 2014 for corresponding Japanese Patent Application No. 2013-015286, 3 pages.
Partial Search Report from Counterpart European Patent Application No. 14182390.6, dated Nov. 17, 2014, 6 pp.
English translation of Russian Office Action, dated May 7, 2014 for corresponding Russian Patent Application No. 2013-100914il4 (001114), 5 pages.
Notice of Preliminary Rejection, and translation thereof, from Counterpart Korean Patent Application No. 10201311847, dated Oct. 23, 2014, 4 pp.
Notice of Reasons for Rejection, and translation thereof, from Counterpart Japanese Patent Application No. 2013015286, dated Oct. 7, 2014, 7 pp.
Notification of the First Office Action, and translation thereof, from Counterpart Chinese Patent Application No. 201310041081.5, dated Nov. 15, 2015, 21 pp.
Extended European Search Report from counterpart European Patent Application No. 15194055.8, dated Mar. 8, 016,7 pp.
Second Office Action, and translation thereof, from counterpart Chinese Application No. 201310041081.5, dated Jul. 24, 2015, 17 pp.
Third Office Action, and translation thereof, from counterpart Chinese Application No. 201310041081.5, dated Feb. 5, 2016, 16 pp.

(56) References Cited

OTHER PUBLICATIONS

Notice of Reasons for Rejection and translation thereof, from counterpart Japanese Application No. 2016-003234, dated Nov. 21, 2016, 12 pp.
Notice of Final Rejection, and translation thereof, from counterpart Japanese Patent Application No. 2013-015286, dated Sep. 7, 2015, 8 pp.
Office Action from counterpart Canadian Patent Application No. 2,889,591, dated Feb. 25, 2016, 3 pp.
Extended European Search Report dated Mar. 13, 2015 in corresponding EP Application No. 14182390.6, 7 pgs.
European Search Report dated Jun. 12, 2013 from corresponding EP Application No. EP 13150274.2 (6 pgs.).
Prosecution History from U.S. Appl. No. 13/364,772, dated Jun. 12, 2013, through Jun. 29, 2018, 109 pp.
First Examination Report from counterpart Indian Patent Application No. 98/DEL/2013, dated May 4, 2018, 7 pp.

* cited by examiner

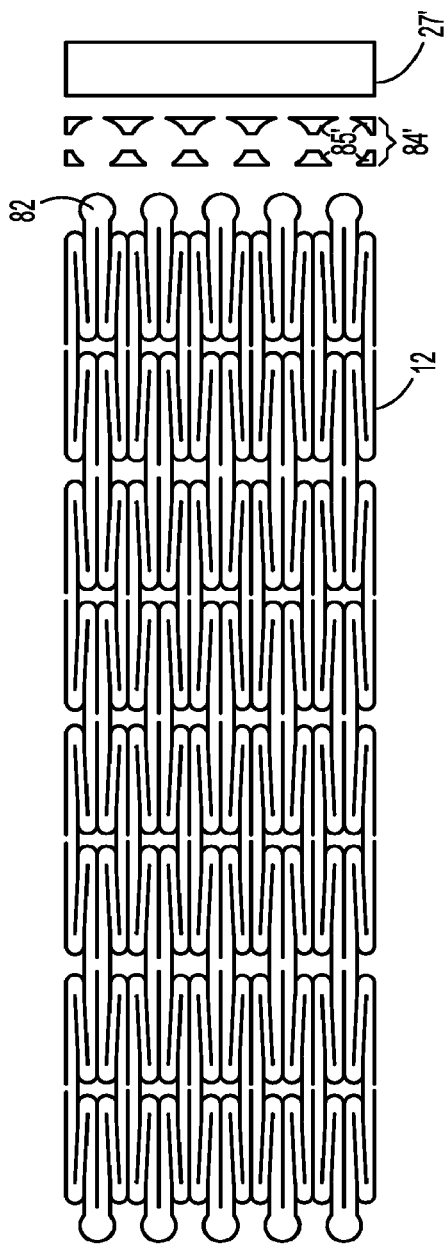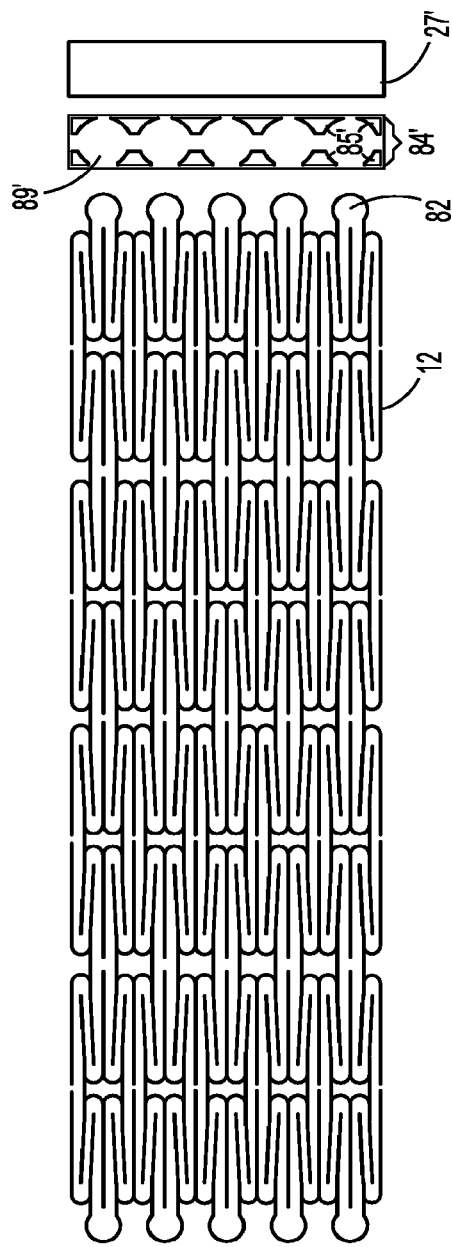

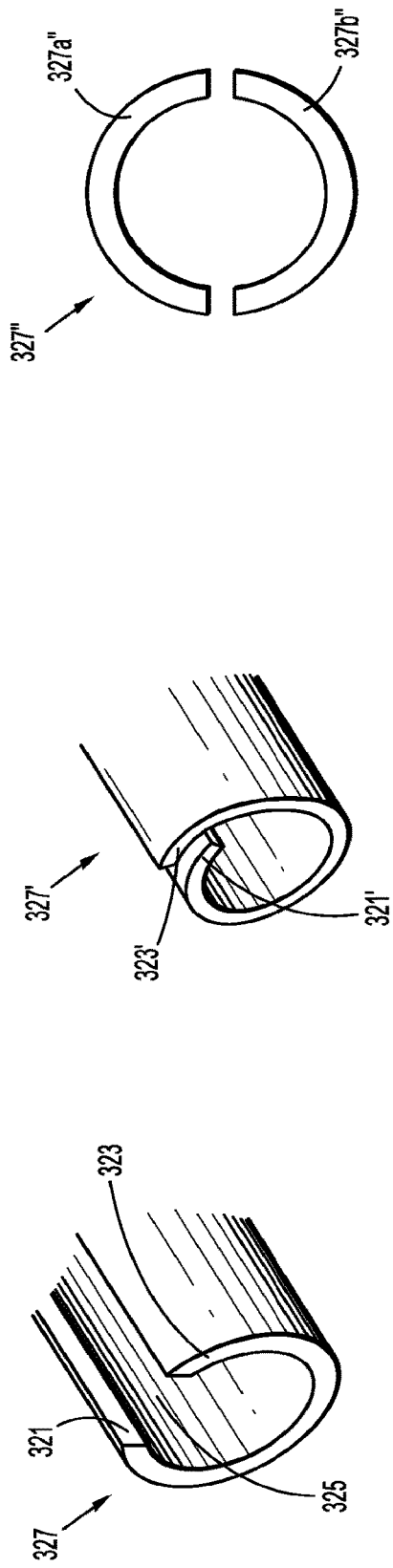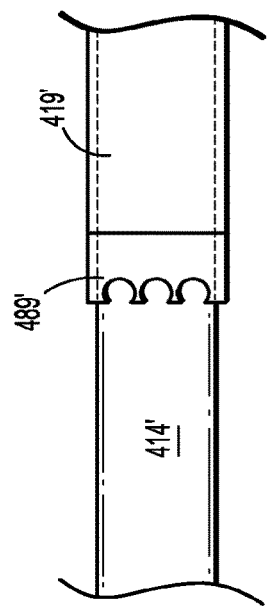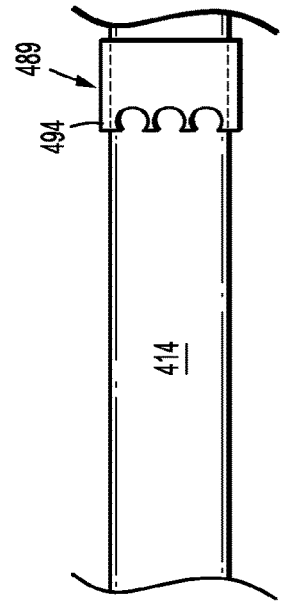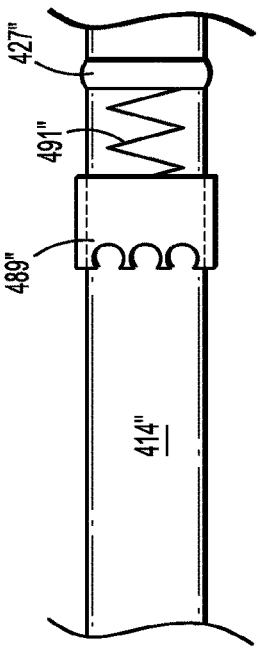

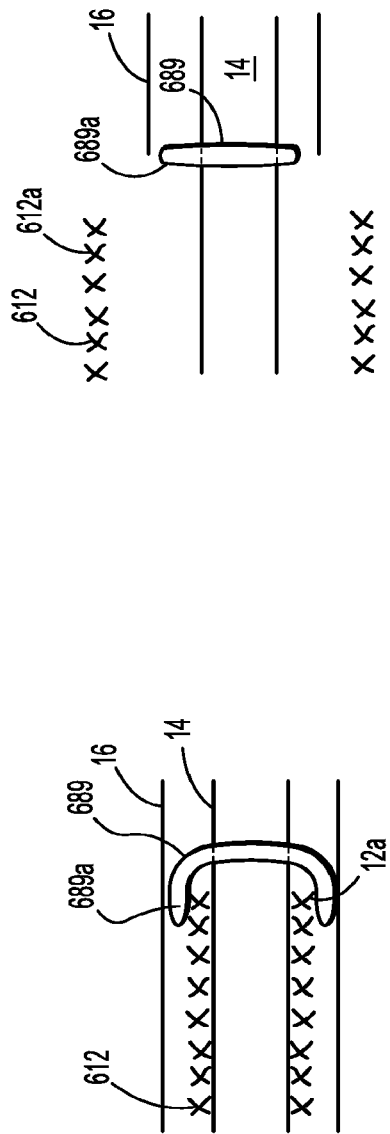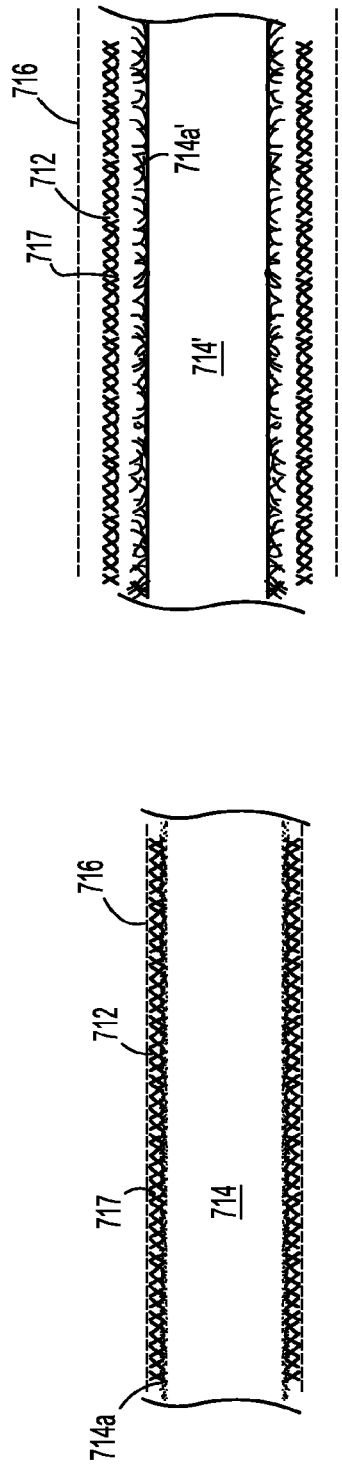

STENT RETAINING SYSTEMS

This application is a continuation of U.S. patent application Ser. No. 13/364,772, filed Feb. 2, 2012, the entire content of which is incorporated herein by reference.

BACKGROUND

1. Field of the Disclosure

The present disclosure relates to a system for delivering an implant to a site in a body lumen. More particularly, the present disclosure relates to a delivery system for a self-expandable implant such as a stent.

2. Description of the Related Art

Stents are widely used for supporting a lumen structure in a patient's body. For example, stents may be used to maintain patency of a coronary artery, other blood vessel, or other body lumen.

Commonly, stents are metal tubular structures. Stents are passed through the body lumen in a collapsed state. At the point of an obstruction or other deployment site in the body lumen, the stent is expanded to an expanded diameter to support the lumen at the deployment site.

In certain designs, stents are open-celled tubes which are expanded by inflatable balloons at the deployment site. Other stents are so-called "self-expanding" stents. Self-expanding stents do not use balloons or other applications of force to cause the expansion of a stent in a collapsed state. An example of a self-expanding stent is a coil structure which is secured to a stent delivery device under tension in a collapsed state. At the deployment site, the coil is released so that the coil can expand to its enlarged diameter. Other self-expanding stents are made of so-called shape-memory metals such as nitinol. Such shape-memory stents experience a phase change at the elevated temperature of the human body. The phase change results in expansion from a collapsed state to an enlarged state.

A delivery technique for shape-memory alloy stents is to mount the collapsed stent on a distal end of a stent delivery system. Such a system would include an outer tubular member and an inner tubular member. The inner and outer tubular members are axially slideable relative to one another. The stent (in the collapsed state) is mounted surrounding the inner tubular member at its distal end. The outer tubular member (also called the outer sheath) surrounds the stent at the distal end.

Prior to advancing the stent delivery system through the body lumen, a guide wire is first passed through the body lumen to the deployment site. The inner tube of the delivery system is hollow throughout its length such that it can be advanced over the guide wire to the deployment site.

The combined structure (i.e., stent mounted on stent delivery system) is passed through the patient's lumen until the distal end of the delivery system arrives at the deployment site within the body lumen. The deployment system may include radiopaque markers to permit a physician to visualize positioning of the stent under fluoroscopy prior to deployment.

At the deployment site, the outer sheath is retracted to expose the stent. The exposed stent is now free to expand within the body lumen. Following expansion of the stent, the inner tube is free to pass through the stent such that the delivery system can be removed through the body lumen leaving the stent in place at the deployment site.

In prior art devices, the stent may prematurely deploy as the outer tube is retracted. Namely, with the outer tube partially retracted, the exposed portion of the stent may expand resulting in the remainder of the stent being squeezed out of the outer tube. This can result in the stent being propelled distally beyond a desired deployment site. Also, once the stent is partially unsheathed, it is sometimes determined that the stent placement needs to be adjusted. With existing systems, this is difficult since the stent has a tendency to force itself out of the sheath thereby making adjustments difficult.

It would be advantageous to provide a system that retains the stent on the catheter even when a majority of the stent has been exposed by retraction of the sheath and that allows a stent to be re-sheathed even after a majority of the stent has been exposed by retraction of the sheath.

The present disclosure provides improved structures for self-expandable implant delivery systems such as stent delivery systems.

SUMMARY

In accordance with an aspect of the present disclosure, a stent delivery system includes an expandable stent, a catheter, and a sheath. The expandable stent includes proximal and distal ends, and a first interlock structure. The catheter includes an elongated member having a second interlock structure displaceably arranged about an outer surface thereof for engaging the first interlock structure of the stent. The sheath is mounted on the elongated member and is positionable in a transport position in which the sheath covers the stent mounted on the elongated member and a deploy position in which the stent is exposed.

In embodiments, the second interlock structure is freely moveable along a longitudinal length of the elongated member. In other embodiments, the movement of the second interlock structure is limited over a predetermined length of the elongated member.

The second interlock structure may be unattached to the elongated member. In some embodiments, the second interlock structure may be attached to an intermediate tube disposed between the elongated member of the catheter and the sheath. In other embodiments, the second interlock structure may be attached to the elongated member by a flexible structure, such as a spring, that allows the second interlock structure to move a predetermined distance along the elongated member.

The second interlock structure may be positioned on a floating retaining ring. The floating retaining ring may be a continuous or discontinuous ring extending completely or partially around the elongated member.

In accordance with another aspect of the present disclosure, a stent delivery system includes an expandable stent, a catheter, and a sheath. The expandable stent includes a plurality of interconnected cells extending between a proximal end and a distal end. The catheter includes an elongated member having a stent mounting location and includes a deformable retaining ring disposed around the elongated member. The sheath is mounted on the elongated member and is positionable in a transport position in which the sheath covers the stent mounted on the elongated member and a deploy position in which the stent is exposed. The deformable retaining ring defines a diameter that is larger than a diameter of the sheath such that when the sheath is in the transport position an outer edge of the deformable retaining ring overlies the proximal end of the stent. The deformable retaining ring may be fabricated from a foam or an elastomer. The deformable retaining ring may be a continuous or discontinuous ring extending completely or partially around the elongated member.

In accordance with yet another aspect of the present disclosure, a stent delivery system includes an expandable stent, a catheter, and a sheath. The expandable stent includes a plurality of interconnected cells extending between a proximal end and a distal end. The catheter includes an elongated member having a stent mounting location including a compressible material. The sheath is mounted on the elongated member and is positionable in a transport position in which the sheath covers the stent mounted on the elongated member such that the cells of the stent are pressed into and capture the compressible material, and a deploy position in which the stent is exposed. The compressible material may be a foam or an elastomer. In embodiments, the stent attachment location of the elongated member may include fibers extending radially therefrom, such that when the sheath is in the transport position, the fibers are captured by the cells of the stent.

BRIEF DESCRIPTION OF THE DRAWINGS

Embodiments of the present disclosure will be better appreciated by reference to the drawings wherein:

FIG. 7A is a laid flat, plan view of a stent having an interlock structure that interlocks with an interlock structure of an inner tube in accordance with an embodiment of the present disclosure;

FIG. 7B is a laid flat, plan view of a stent having an interlock structure that interlocks with an interlock structure of a retaining ring of an inner tube in accordance with another embodiment of the present disclosure;

FIGS. 11A and 11B are perspective view of a retaining structure for the interlock structure of the inner tube in accordance with embodiments of the present disclosure;

FIG. 11C is an end view of a retaining structure for the interlock structure of the inner tube in accordance with embodiments of the present disclosure;

FIG. 12A is a side view of a floating interlock structure of an inner tube in accordance with an embodiment of the present disclosure;

FIG. 12B is a side view of a floating interlock structure of an inner tube in accordance with another embodiment of the present disclosure;

FIG. 12C is a side view of a floating interlock structure of an inner tube in accordance with yet another embodiment of the present disclosure;

FIGS. 15A and 15B are schematic cross-sectional illustrations of an interlock structure of a stent and an inner tube with the stent positioned in a compressed and expanded state, respectively, in accordance with an embodiment of the present disclosure;

FIG. 16A is a schematic cross-sectional illustration of an interlock structure of an inner tube interlocked with a stent in accordance with an embodiment of the present disclosure; and FIG. 16B is a schematic cross-sectional illustration of an interlock structure of an inner tube in accordance with another embodiment of the present disclosure.

DETAILED DESCRIPTION

Figure 1:
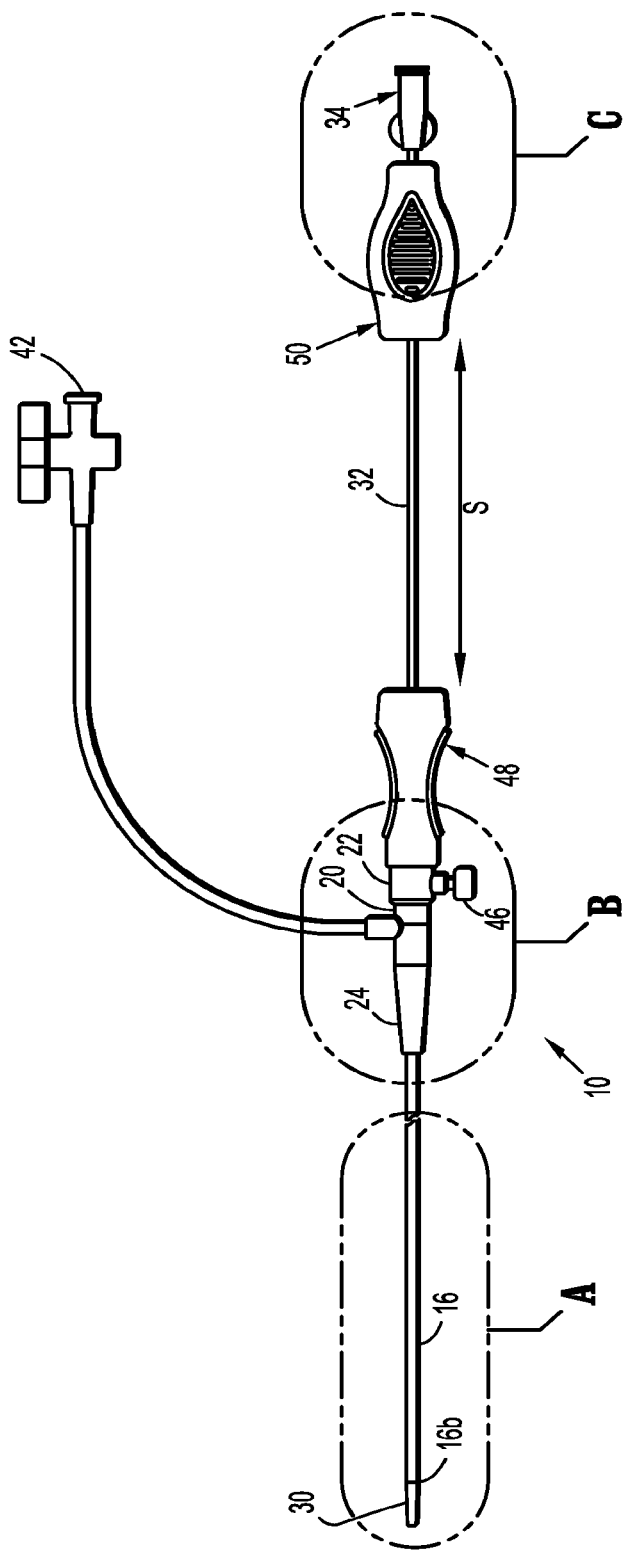
FIG. 1 is a side elevation view of a stent delivery system according to principles of the present disclosure.

Various exemplary embodiments of the present disclosure will be discussed hereinbelow in terms of a stent delivery system equipped with an interlock configuration that constrains relative axial movement of a stent about an inner tube until after the outer tube has been fully retracted. It should be understood that a variety of stent delivery systems may be utilized with the embodiments of the interlock configuration of the present disclosure.

Embodiments of the presently disclosed stent delivery system will now be described in detail with reference to the drawing figures wherein like reference numerals identify similar or identical elements. In the following discussion, the terms "proximal" and "trailing" may be employed interchangeably, and should be understood as referring to the portion of a structure that is closer to a clinician during proper use. The terms "distal" and "leading" may also be employed interchangeably, and should be understood as referring to the portion of a structure that is further from the clinician during proper use. As used herein, the term "patient" should be understood as referring to a human subject or other animal, and the term "clinician" should be understood as referring to a doctor, nurse or other care provider and may include support personnel.

With initial references to FIGS. 1-4, an exemplary stent delivery system 10 is shown. The stent delivery system 10 is for delivery of a stent 12 to a deployment site in a body lumen of a patient's body. By way of non-limiting, representative example, the stent 12 may be a self-expanding, open-celled, tubular stent having a construction such as that shown in U.S. Pat. No. 6,132,461, which is hereby incorporated by reference, and formed of a self-expanding, shape-memory or superelastic metal such as nitinol, or the like. The stent 12 may also be a coil stent, any other self-expanding stent, or a balloon expandable stent such as that shown in U.S. Pat. No. 6,827,732, which is hereby incorporated by reference. The stent 12 includes a proximal end 12a and a distal end 12b. Another representative stent is shown in U.S. Pat. No. 6,558,415, which is hereby incorporated by reference.

Figure 2A:
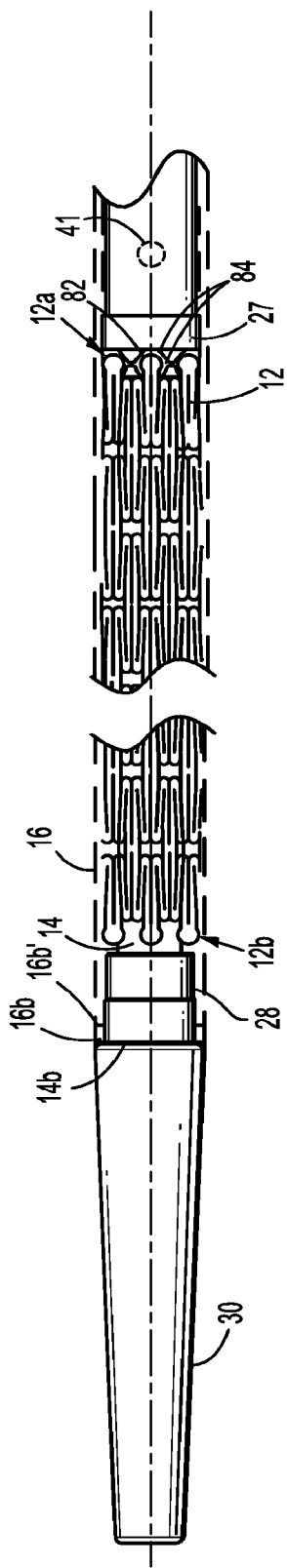
FIG. 2A is an enlarged cross-sectional view of detail A of FIG. 1 with the stent in a compressed orientation.

The stent 12 is carried on the stent delivery system 10 in a collapsed (or reduced diameter) state as shown in FIG. 2A. Upon release of the stent 12 from the stent delivery system 10 (as will be described), the stent 12 expands to an enlarged diameter (see FIG. 2B) to abut against the walls of the patient's lumen in order to support patency of the lumen.

The stent delivery system 10 includes an inner tubular member 14 (i.e., also referred to as an elongated member) and an outer tubular member 16. Both of the inner and outer tubular members 14 and 16 extend from proximal ends 14a, 16a to distal ends 14b, 16b.

The outer tubular member 16 is sized to be axially advanced through the patient's body lumen. In embodiments, the tubular member 16 is sufficiently long for the distal end 16b to be placed near the deployment site in the patient's body lumen with the proximal end 16a remaining external to the patient's body for manipulation by a clinician. By way of example, the outer tubular member 16 (also referred to as a sheath) may be a braid-reinforced polyester of tubular construction to resist kinking and to transmit axial forces along the length of the sheath 16. The outer tubular member 16 may be of widely varying construction to permit varying degrees of flexibility of the outer tubular member 16 along its length.

Figure 3:
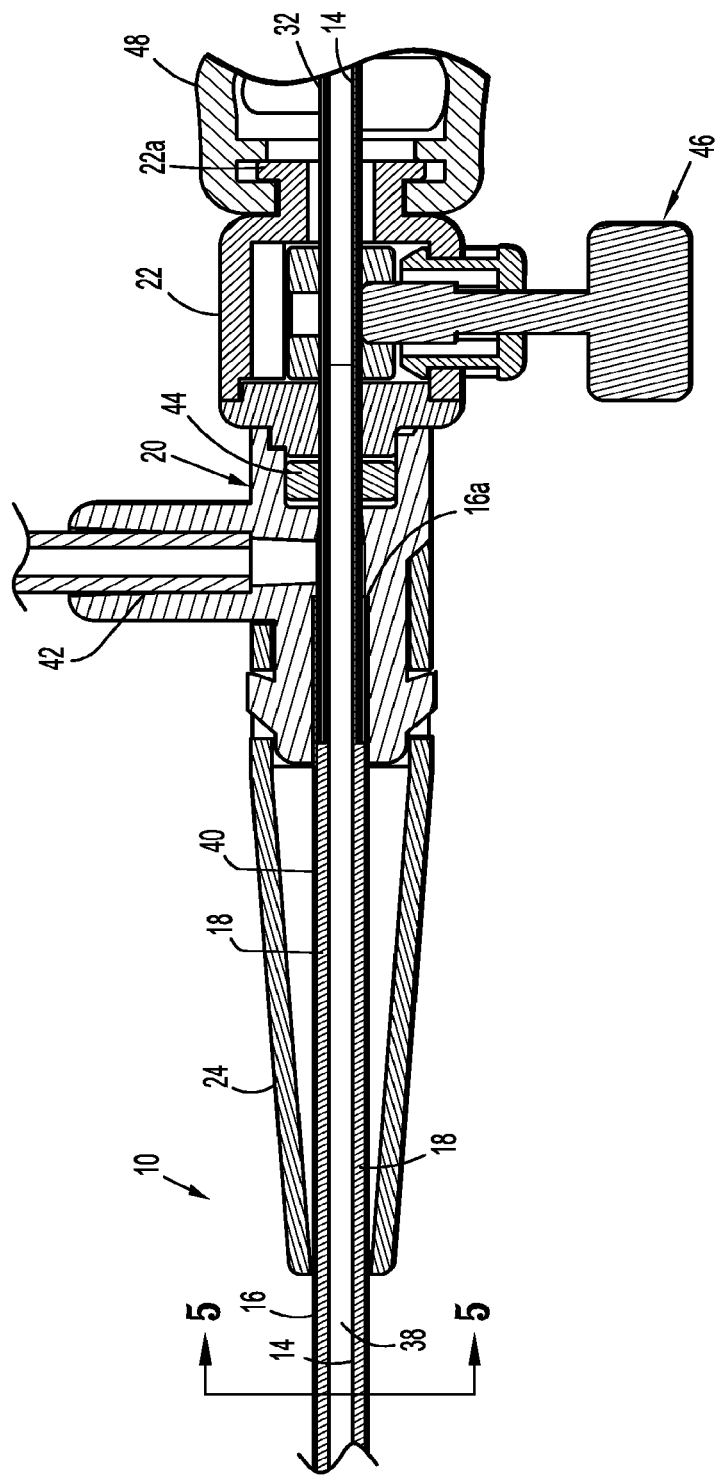
FIG. 3 is an enlarged cross-sectional view of detail B of FIG. 1.

As shown in FIG. 3, the proximal end 16a of the outer tubular member 16 is bonded to a manifold housing 20. The manifold housing 20 is threadedly connected to a lock housing 22. A strain relief jacket 24 is connected to the manifold housing 20 and surrounds the outer tubular member 16 to provide strain relief for the outer tubular member 16.

Figure 2B:
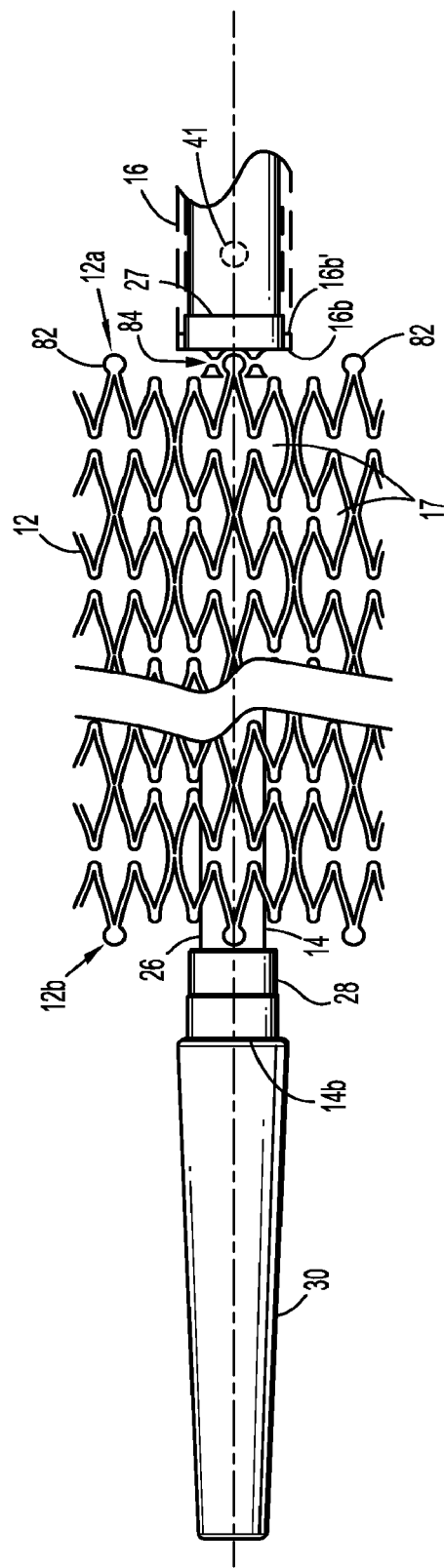
FIG. 2B is an enlarged cross-sectional view of detail A of FIG. 1 with the stent in a deployed (i.e., expanded) orientation.

In embodiments, the inner tubular member 14 is formed of nylon but may be constructed of any suitable material. As shown in FIG. 2B, the inner tubular member 14 defines a stent attachment location 26. The inner tubular member 14 also includes radiopaque markers 27, 28 that are attached to an outer surface of the inner tubular member 14 (e.g., by techniques such as adhesive, heat fusion, interference fit, or other techniques). The attachment location 26 is positioned between the radiopaque markers 27, 28. The radiopaque markers 27, 28 permit a clinician to accurately determine the position of the stent attachment location 26 within the patient's lumen under fluoroscopic visualization. As will be described later in the specification, in some embodiments, at least one of the markers 27, 28 forms a collar including a geometry that interlocks with the stent 12 to prevent axial movement of the stent 12 relative to the inner tubular member during transport and deployment of the stent 12. In other embodiments, markers 27, 28 are positioned on the proximal end 12a and/or distal end 12b of the stent 12.

A tapered and flexible distal tip member 30 is secured to the distal end 14b of the inner tubular member 14. The highly flexible distal tip member 30 permits advancement of the stent deployment system 10 through the patient's lumen and minimizes trauma to the walls of the patient's lumen.

Figure 4:
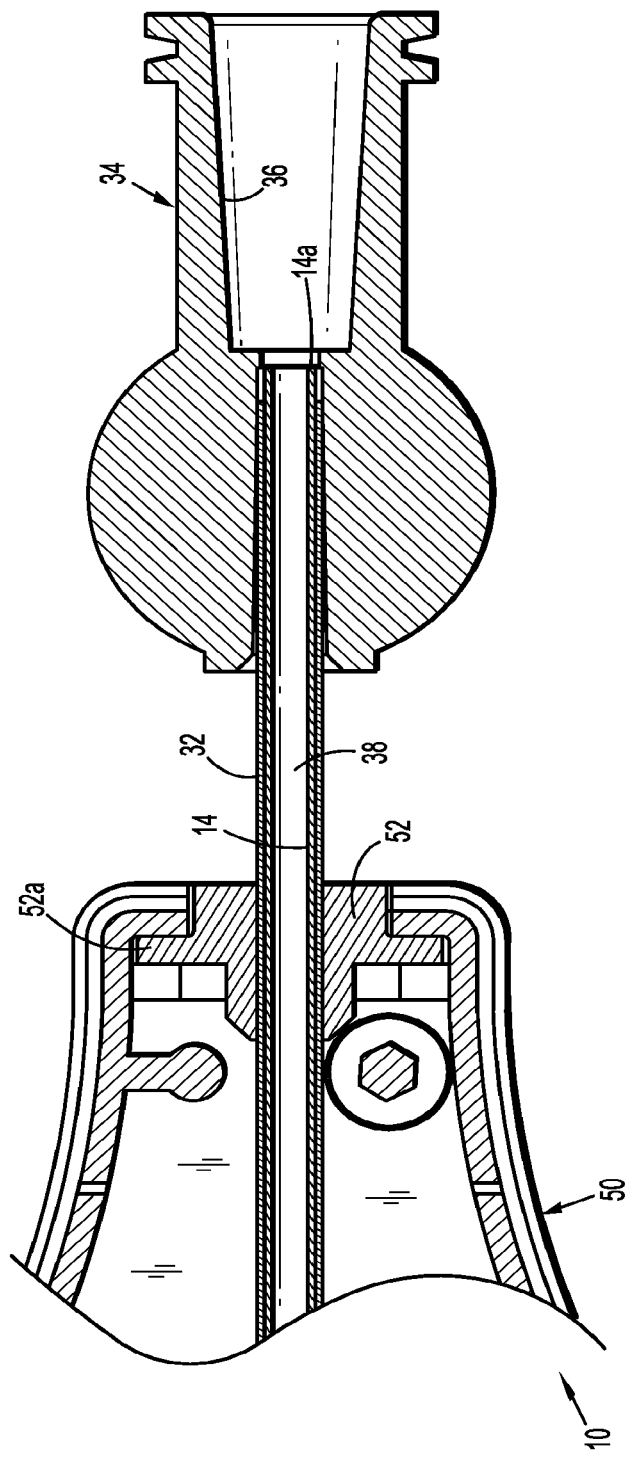
FIG. 4 is an enlarged cross-sectional view of detail C.

As best shown in FIGS. 3 and 4, the inner tube 14 passes through both the manifold housing 20 and lock housing 22. A stainless steel jacket 32 surrounds and is bonded to the inner tubular member 14. At the inner tube proximal end 14a, a port housing 34 is bonded to the stainless steel jacket 32. The port housing 34 has a tapered bore 36 aligned with an inner lumen 38 of the tubular member 14. The inner lumen 38 extends completely through the inner tubular member 14 so that the entire delivery system 10 can be passed over a guide wire (not shown) initially positioned within the patient's lumen. Opposing surfaces of the inner and outer tubular members 14 and 16, define a first lumen 40 (best seen in FIG. 5). As described in U.S. Pat. No. 6,623,491, which is hereby incorporated by reference, splines 18 can be provided between the inner and outer tubular members 14 and 16.

As shown in FIG. 3, the manifold housing 20 carries an admission port 42 for injecting a contrast media into the interior of the manifold housing 20. The interior of the manifold housing 20 is in fluid flow communication with the first lumen 40. Discharge ports 41 (shown in FIGS. 2A and 2B) are formed through the outer tubular member 16 to permit contrast media to flow from the first lumen 40 into the patient's body lumen.

As shown in FIG. 3, an O-ring 44 surrounds the stainless steel jacket 32 between the manifold housing 20 and lock housing 22. Upon threaded connection of the manifold housing 20 to the lock housing 22, the O-ring 44 compresses against the stainless steel jacket 32 in sealing engagement to prevent contrast media from flowing in any path other than through the first lumen 40.

As shown in FIGS. 1 and 3, the lock housing 22 carries a threaded locking member (or lock nut) 46 which can be turned to abut the stainless steel jacket 32. The lock nut 46 can be released to free the stainless steel jacket to move axially. According, when the lock nut 46 engages the jacket 32, the jacket 32 (and attached inner tubular member 14) cannot move relative to the lock housing 22, manifold housing 20, or the outer tubular member 16. Upon release of the lock nut 46, the inner tubular member 14 and outer tubular member 16 are free to slide axially relative to one another between a transport position and a deploy position.

First and second handles 48, 50 are secured to the lock housing 22 and jacket 32, respectively. In the transport position (shown in FIG. 2A), the handles 48, 50 are spaced apart and the distal end of the outer tubular member 16 forms a sheath that covers the stent attachment location 26 to prevent premature deployment of the stent 12. When the handle 48 is pulled rearwardly toward the handle 50, the outer tubular member 16 slides rearwardly or proximally relative to the inner tubular member 14. In embodiments, the outer tubular member 16 slides rearwardly a distance sufficient to fully expose the stent attachment location 26 and permit the stent 12 to freely expand toward its fully expanded diameter (see FIG. 2B). After such expansion, the stent delivery system 10 can be proximally withdrawn through the expanded stent 12 and removed.

As shown in FIG. 3, the first handle 48 is rotatably mounted on a flange 22a of the lock housing 22. The first handle 48 surrounds the stainless steel jacket 32 and is freely rotatable about the longitudinal axis of the jacket 32 and freely rotatable about the flange 22a. The first handle 48 is axially affixed to the lock housing 22 such that axial forces applied to the first handle 48 are transmitted through the lock housing 22 and manifold housing 20 to the outer tubular member 16 to axially move the outer tubular 16. However, rotary action of the first handle 48 about the axis of the stainless steel jacket 32 is not transmitted to the housings 20, 22 or to the outer tubular member 16 by reason of the free rotation of the first handle 48 on flange 22a.

As shown in FIG. 4, the second handle 50 is mounted on an anchor 52 that is bonded to the stainless steel jacket 32 through any suitable means (such as by use of adhesives). The anchor 52 includes a flange 52a that is radial to the axis of the stainless steel jacket 32. The second handle 50 is mounted on the flange 52a and is free to rotate on the anchor 52 about the axis of the stainless steel jacket 32. However, axial forces applied to the handle 50 are transmitted to the stainless steel jacket 32 which, being bonded to the inner tubular member 14, results in axial movement of the inner tubular member 14.

With the handle construction described above, relative axial movement between the handles 48, 50 results in relative axial movement between the inner and outer tubular members 14, 16. Rotational movement of either of the handles 48, 50 does not affect rotational positioning of the inner or outer tubular members 14, 16 and does not affect axial positioning of the inner and outer tubes 14, 16.

The free rotation of the handles 48, 50 results in ease of use for a clinician who may position his or her hands as desired without fear of interfering with any axial positioning of the inner and outer tubular members 14, 16. The spacing between the handles 48, 50 is equal to the stroke between the transport position and the deploy position of the tubular members 14, 16. As a result, the spacing permits a clinician to have ready visual indication of the relative axial positioning between the inner and outer tubular members 14, 16. This relative axial positioning can be fixed by engaging the lock nut 46. In any such positioning, contrast media can be injected through the admission port 42 into the chamber 40 with the contrast media flowing out of the side ports 41 into the body lumen to permit visualization under fluoroscopy.

With stent deployment systems having premounted stents of various axial lengths, the positioning of the second handle 50 on the stainless steel jacket 32 can be selected at time of assembly so that a spacing S (see FIG. 1) between the handles 48, 50 corresponds to the length of the stent 12 carried on the stent deployment system. For example, in an embodiment, the spacing S is about 10 millimeters longer than the deployed length of the stent. Accordingly, a clinician will know that the outer tubular member 16 has been fully retracted when the handles 48, 50 have been pushed completely together to completely release the stent 12. Also, the freely rotatable handles 48, 50 are easy to hold from any angle without slippage. The lock nut 46 ensures that the stent 12 will not deploy prematurely.

A concern with existing delivery systems for self-expanding stents is control of stent delivery. For example, due to their elastic characteristics, self-expanding stents have a tendency to propel themselves axially outwardly from their restraining sheaths before the sheaths have been completely retracted. When this occurs, control of stent placement is compromised since the stent may overshoot the desired deployment site. Further, once the stent has been completely deployed, subsequent adjustment of the stent deployment location can be difficult because re-sheathing typically cannot be readily accomplished.

To address the above concerns, the delivery system 10 is equipped with an interlock configuration that constrains relative axial movement between the stent 12 and the inner tube 14 until after the sheath 16 has been fully retracted. For example, when the stent 12 is mounted on the inner tube 14 and restrained in the compressed orientation by the sheath 16 as shown in FIG. 2A, a first interlock structure 82 (e.g., a continuous ring as shown in FIG. 2A) located at the proximal end of the stent 12 interlocks with a second interlock structure 84 (e.g., a plurality of protuberances as shown in FIG. 2A) defined by the proximal marker 27 (also referred to as a collar). The interlock geometries remain interlocked to constrain axial movement of the stent 12 until after the sheath 12 has been retracted beyond a predetermined location (e.g., the proximal-most end 12a of the stent 12). When the sheath 12 has been retracted beyond the predetermined location, the first interlock structure 82 of the stent 12 is allowed to expand. As the stent 12 expands, the first interlock structure 82 of the stent 12 disengages from the second interlock structure 84 of the marker 27 thereby allowing the inner tube 14 of the catheter to be moved axially relative to the stent 12 without interference from the first and second interlock structures 82, 84.

Figure 6C:
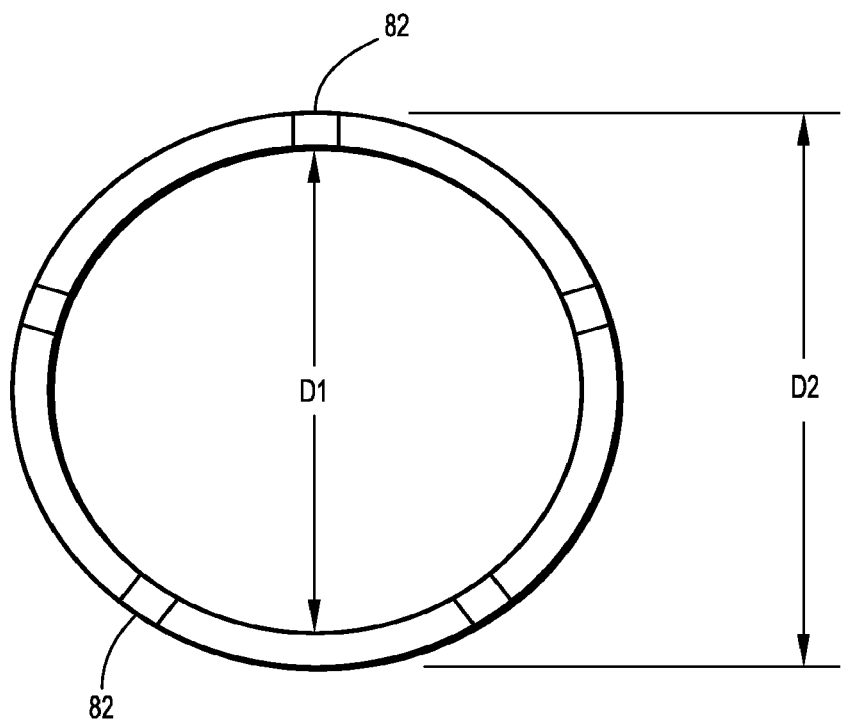
FIG. 6C is an end view of the stent of FIGS. 6A and 6B in its tubular configuration.
Figure 6A:
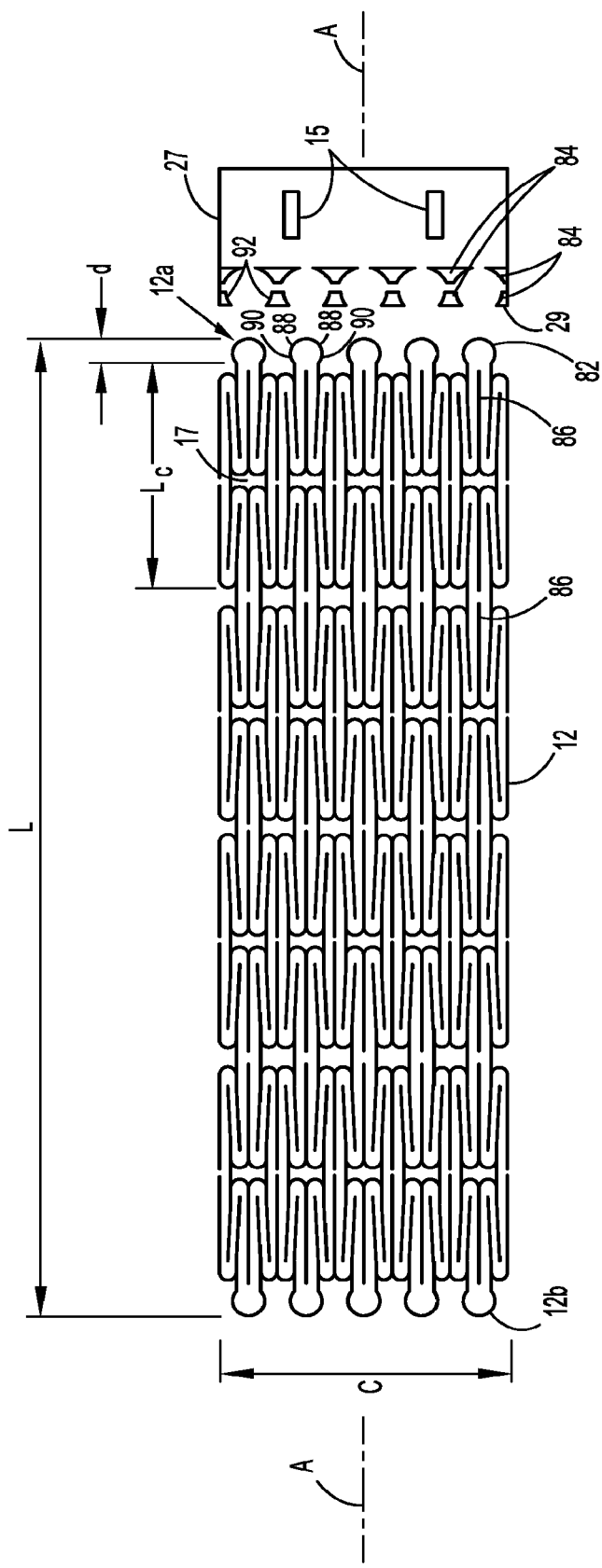
FIG. 6A is a plan view of a first stent having an interlock structure that interlocks with an interlock structure of a collar of an inner tube, the stent and a collar are shown cut longitudinally and laid flat with an axial separation between the stent proximal end and the collar.
Figure 6B:
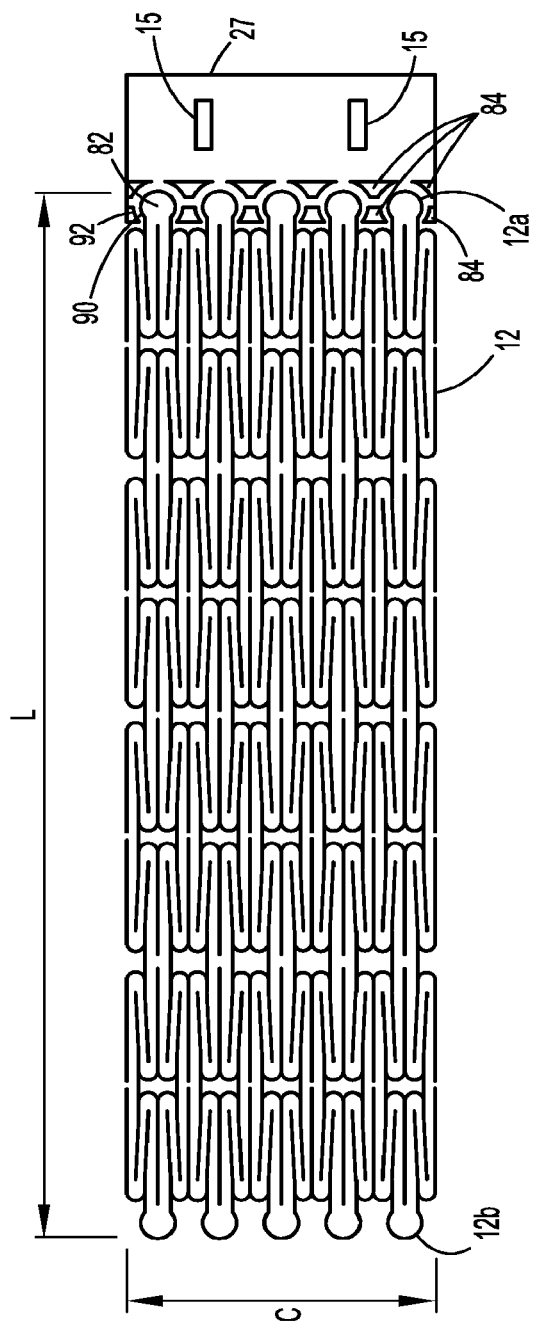
FIG. 6B is the view of FIG. 6A with the stent proximal end and collar shown interlocked.

FIGS. 6A and 6B illustrate the proximal end 12a of the stent 12 in relation to the marker 27 located at the proximal end of the attachment location 26. In FIGS. 6A and 6B, the stent 12 and the marker 27 have been cut longitudinally and laid flat. The stent 12 has a length L and a circumference C. In FIG. 6A, the marker 27 and the stent 12 are shown disengaged from one another. In FIG. 6B marker 27 and the stent 12 are shown interlocked.

Referring to FIG. 6A, the stent 12 includes a plurality of struts 86 (i.e., reinforcing members). A number of the plurality of struts, e.g. twelve, define a cell 17 (also shown in FIG. 2B). The stent 12 is made up of a plurality of interconnected cells 17. Still referring to FIG. 6A, each cell has a compressed or collapsed cell length Lc. At least some of the struts 86 of the cells 17 have free terminal ends that define the proximal and distal ends 12a and 12b of the stent 12. First interlock structures 82 (i.e., keys) are provided at the free terminal ends of the struts 86. As shown in FIG. 6A, the first interlock structures 82 include enlargements in the form of circular projections that extend a distance d from the free terminal ends of the struts 86. In embodiments, the distance d that the first interlock structures 82 extends from the free terminal ends of the struts 86 is less than the collapsed cell length Lc of the cells 17. Thus, the first interlock structures 82 are within at most one collapsed cell length Lc of the cells 17.

The circular projections of the first interlock structures 82 include interlock portions 88 that project outwardly from the struts 86 in a circumferential direction (i.e., in a direction coinciding with the circumference C of the stent 12). The interlock portions 88 include interlock surfaces 90 that face in an axial direction. The phrase "face in an axial direction" will be understood to mean that least a vector component of the surface 90 is perpendicular with respect to a longitudinal axis A-A of the stent 12. Thus, the surface 90 need not be completely perpendicular relative to the longitudinal axis of the stent 12 to be construed as facing in an axial direction. In other words, a surface aligned at oblique angle relative to the longitudinal axis of the stent 12 shall also be construed as facing in an axial direction since such surface has a vector component that is perpendicular relative to the longitudinal axis of the stent.

As best shown schematically in FIG. 6C, the first interlock structures 82 are positioned within a region defined between an inner diameter D1 and an outer diameter D2 of the stent 12. In embodiments, at least portions of the interlock surfaces 90 are located within 5 millimeters of the proximal end 12a of the stent 12. In some embodiments, at least portions of the interlock surfaces 90 are located within 3 millimeters of the proximal end 12a of the stent 12. In yet other embodiments, at least portions of the interlock surfaces 90 are located within 2 millimeters of the proximal end 12a of the stent 12.

Still referring to FIGS. 6A and 6B, the radiopaque marker 27 has an axial distal edge 29 facing the proximal end 12a of stent 12. Second interlock structures 84 (i.e., discontinuous sockets, openings, keyways, etc.) are at least partially defined by the radiopaque marker 27. Each of the second interlock structures 84 includes interlock surfaces 92 that face in an axial direction. The second interlock structures 84 are configured to have a complementary mating geometry with respect to the first interlock structures 82 of the stent 12. For example, similar to the first interlock structures 82, the second interlock structures 84 are shown having generally rounded or circular shapes. By "complementary", it is meant that the mating geometry of the interlock configuration need not have identical or substantially identical complementary shapes, but rather, to provide an interlock, it is only necessary for a portion of the first interlock structure 82 to be received in the second interlock structure 84, or vice versa, such that mechanical interference or overlap between the first and second interlock structures 82, 84 prevents the interlocks from being axially separated.

The geometry of the second interlock structures 84 is selected to mate with the predetermined geometry of the proximal end 12a of the stent 12 such that the stent 12 and the marker 27 can be axially coupled or interlocked when the stent 12 is compressed at the mounting location 26. When the first and second interlock structures 82 and 84 are interlocked, the interlock surfaces 90 and 92 oppose and circumferentially overlap one another (see FIG. 6B) such that the stent 12 is restricted from distal movement relative to the marker 27.

With the specific embodiment shown, the stent 12 and collar 27 are rotary coupled such that the stent 12 and collar 27 are restricted from relative rotary motion (i.e., about axis A-A) when the stent 12 is in the collapsed state. The predetermined stent geometry of the first interlock structures 82 and the complementary mating geometry of the second interlock structures 84 of the collar 27 do not restrict relative radial motion. Namely, as the self-expanding stent 12 expands radially, the first interlock structures 82 are free to radially move out of the second interlock structures 84. After such motion, the stent 12 is no longer coupled to the collar 27 and the stent 12 and collar 27 are free to move axially, radially, or transversely to one another.

With the embodiment thus described, the mating features of the stent 12 and collar 27 prevent premature discharge of the stent 12 from a stent attachment location 26. As the outer sheath 16 is retracted, the sheath distal end 16b exposes the distal end 12b of the stent 12. At this point, the exposed distal end 12b of the stent 12 is free for limited expansion restrained by the remainder of the stent 12 being covered by the sheath 16 and by the attachment of the stent proximal end 12a to the proximal radiopaque marker 27.

Further retraction of the sheath 16, permits still further expansion of the stent 12. As the sheath distal end 12b approaches the stent proximal end 12a, the expansion of the stent material tends to urge the stent 12 to squeeze out of the small portion of the sheath 16 now covering the stent 12. However, this propensity is overcome by the attachment of the stent proximal end 12a to the collar 27 since any such ejection of the stent 12 would require axial separation of the stent 12 and collar 27. Such movement is prevented by the first interlock structures 82 and the second interlock structures 84.

Therefore, as long as any portion of the sheath 16 overlies the first and second interlock structures 82 and 84, the proximal end 12a of the stent 12 cannot expand and cannot axially move away from the collar 27. Accordingly, the stent 12 is not released from the attachment location 26 until a clinician has fully retracted the sheath 16 with the sheath distal end 16b retracted proximal to the proximal end of stent attachment location 26. The sheath distal end 16b is provided with a radiopaque marker 16b' (shown in FIGS. 2A and 2B) to permit visualization of the relative position of the sheath distal end 12b and the radiopaque markers 27, 28 of the stent attachment location 26.

With the structure and operation thus described, a clinician has greater control of the release of the stent 12 and more accurate stent positioning is attained. As long as even a small portion of the sheath 16 is not fully retracted (e.g., at least 1 mm extends distally to the proximal end 12a of the stent 12) the axial position of the stent 12 may be adjusted by advancing or retracting the inner tubular member 14. Also, as long as a small portion of the sheath 16 remains covered by the sheath 16 (e.g., at least 1 mm), the stent 12 may be readily re-sheathed by moving the sheath 16 in a distal direction.

In the embodiment of FIGS. 6A and 6B, the pattern and shape of the first interlock structures 82 and the second interlock structures 84 are symmetrical about the stent axis A-A. As a result, the stent 12 can be affixed to the collar 27 in any one of a plurality of rotary alignments about axis A-A. It will be appreciated that the pattern and shape of interlock structures 82, 84 may vary such that the stent 112 can only be affixed to the collar 27 in a limited or unique mating structure.

Further, the embodiment of FIGS. 6A and 6B shows that the interlock between the stent 12 and the tube 14 is provided at the proximal end 12a of the stent 12b. It will be appreciated that for certain embodiments, the interlock between the inner tube 14 and the stent 12 can be provided at the distal end 12b of the stent 12 (e.g., for a distally retractable sheath). Moreover, while the embodiment of FIGS. 6A and 6B shows interlock structures provided at all of the proximal ends of the struts 86, the interlock structures of the present disclosure are not so limited. For example, in some embodiments, only some of the struts 86 may include interlock structures. While in certain embodiments it may be desirable to use only one interlock structure at the end of the stent 12, in other embodiments, it may be desirable to use at least two separate/discrete interlock structures uniformly spaced about the circumference of the stent. In yet other embodiments, it may be desirable to use at least 4 separate/discrete interlock structures that may be uniformly spaced about the circumference of the stent.

The collar 27 may be provided with indicia to indicate to a clinician the position of the collar 27 (and hence the stent 12) when the combination is in a patient's vessel and is being visualized under fluoroscopy. In the embodiment of FIGS. 6A and 6B, the indicia is shown as cutouts 15 in the collar 27. Other configurations of indicia on or proximal to the collar 27 are envisioned, such as those described in U.S. Pat. No. 6,623,518, which is hereby incorporated by reference.

As described above, the interlock structure 84 of the inner tube 14 is provided on the proximal radiopaque marker 27. It will be appreciated that the interlock structures 84 need not be the same element as the radiopaque marker 27 but could be a separate part. As a separate part, the interlock structures 84 could be integrally formed with, or joined to, the inner tube 14, connected to the outer surface of the inner tube 14 by conventional techniques (e.g., adhesive, fasteners, fusion bonding, etc.), or be connected to the outer surface of the inner tube 14 by one or more intermediate members (e.g., a retaining ring).

FIG. 7A illustrates second interlock structures 84' that include a plurality of protuberances 85' separate from collar 27'. Protuberances 85' are provided on the inner tube and extend radially outward from the inner tube. Protuberances 85' are positioned distal to the collar 27'. Protuberances 85' may be formed from metal, polymer, or other materials and may be fabricated as part of the inner tube (e.g., molded, stamped, etc.) or as separate pieces. In embodiments, protuberances 85' may be part of a single disk-like component built into the inner tube. FIG. 7B illustrates an embodiment of the second interlock structures 84' disposed on a retaining ring 89' joined to an outer surface of the inner tube distal to the collar 27'. It will be appreciated that in embodiments utilizing an interlock structure that is separate from the collar, the collar may be omitted and a radiopaque marker may be provided on the interlock structures themselves, such as on protuberances 85".

Figure 8:
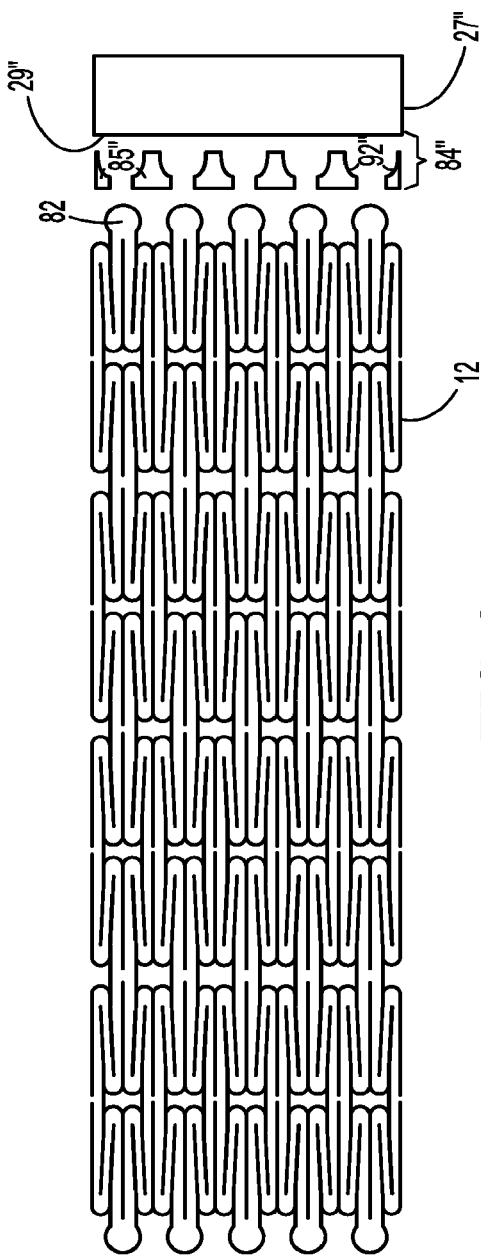
FIG. 8 is a laid flat, plan view of a stent having an interlock structure that interlocks with an interlock structure of an inner tube in accordance with yet another embodiment of the present disclosure.

FIG. 8 illustrates second interlock structures 84" that are formed of protuberances 85" in combination with the collar 27". Second interlock structure 84" includes interlock surfaces 92" defined by surfaces of the protuberances 85" that face in an axial direction. Distal edge 29" of the collar 27" prevents the movement of the stent 12 proximally and aids in preventing the interlocks 82', 84' from being axially separated.

Figure 9A:
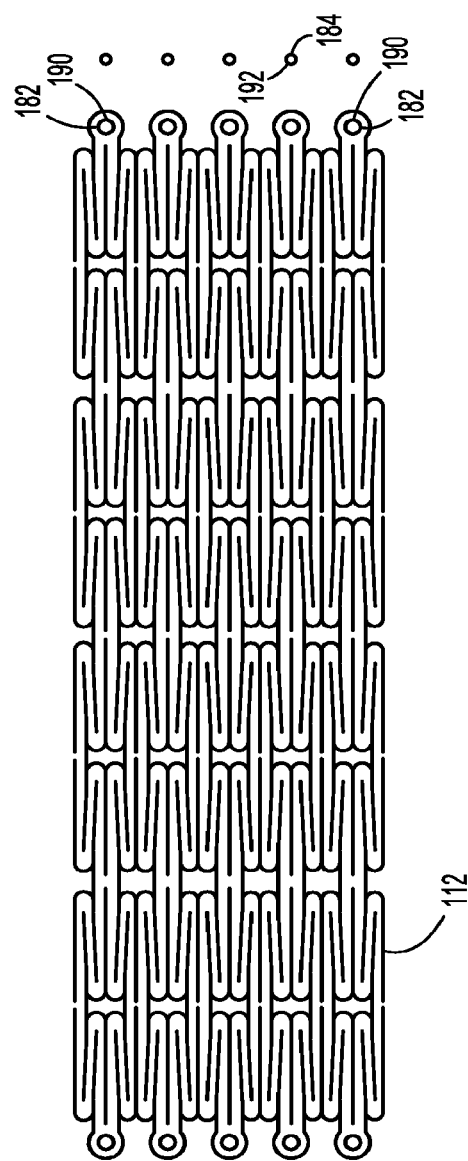
FIG. 9A is a laid flat, plan view of a stent having an interlock structure that interlocks with an interlock structure of an inner tube in accordance with an embodiment of the present disclosure.
Figure 9B:
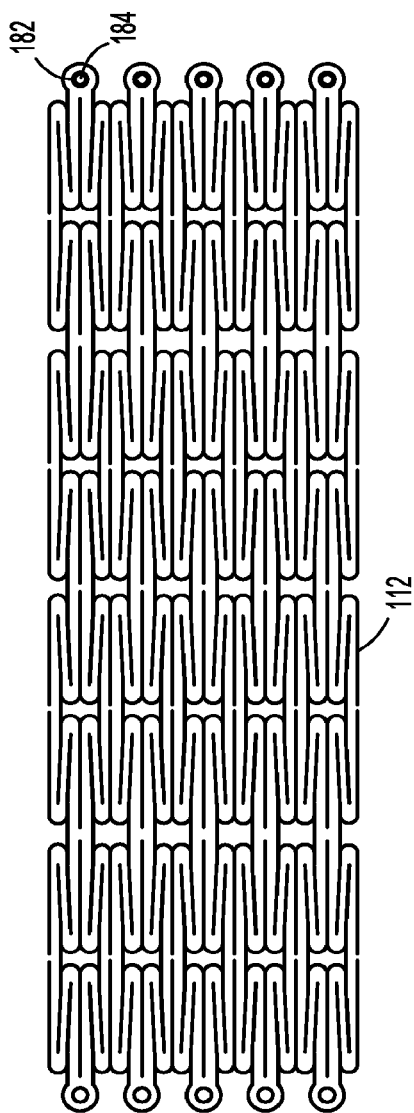
FIG. 9B is the view of FIG. 9A with the mating structures of the stent and inner tube shown interlocked.

FIGS. 9A and 9B illustrate an embodiment of a stent 112 including first interlock structures 182 in the form of circular openings defined through enlarged strut ends of the stent 112. The first interlock structures 182 include distally facing interlock surfaces 190 and are sized to receive second interlock structures 184 in the form of cylindrical posts, pins, or pegs. The posts are connected to the outer surface of the inner tube 14 (e.g., integrally or otherwise), or alternatively, may be connected to a collar or retaining ring. The posts define proximally facing interlock surfaces 192. When the first and second interlock structures 182 and 184 are coupled as shown in FIG. 9B, the surfaces 190 and 192 engage each other to prevent distal movement of the stent 112 relative to the posts.

Figure 9C:
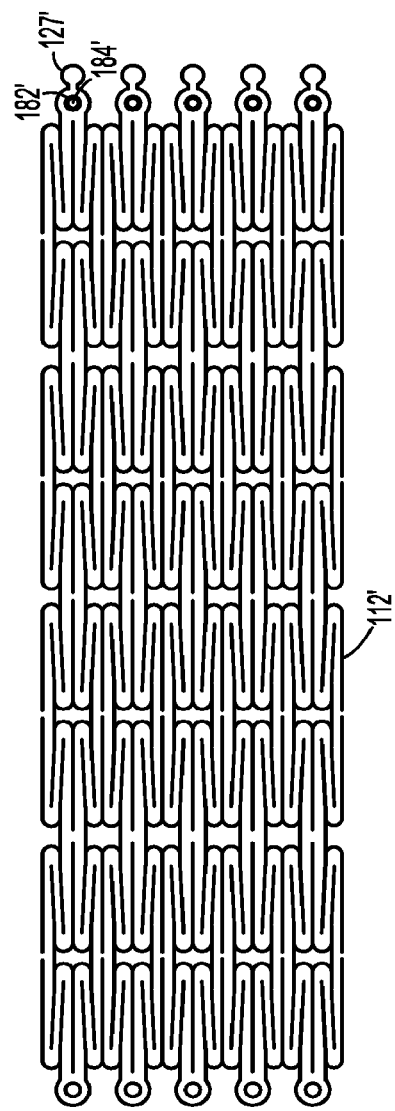
FIG. 9C is a laid flat, plan view of a stent having radiopaque markers and an interlock structure that interlocks with an interlock structure of an inner tube in accordance with another embodiment of the present disclosure.

FIG. 9C illustrates an embodiment of a stent 112' where radiopaque markers 127' are positioned on the proximal end 112a' of the stent 112'. Radiopaque markers 127' include enlargements in the form of circular projections that extend from the free terminal ends of the first interlock structures 182'. It will be appreciated that the radiopaque markers 127' may be of any shape or size.

Figure 10A:
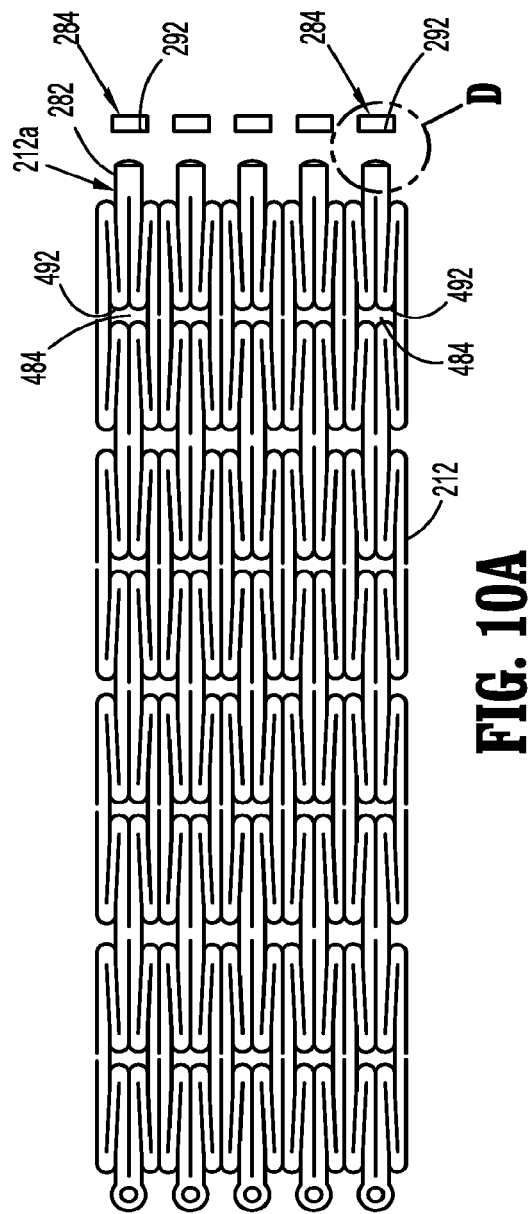
FIG. 10A is a laid flat, plan view of a stent having an interlock structure that interlocks with an interlock structure of an inner tube in accordance with an embodiment of the present disclosure.
Figure 10C:
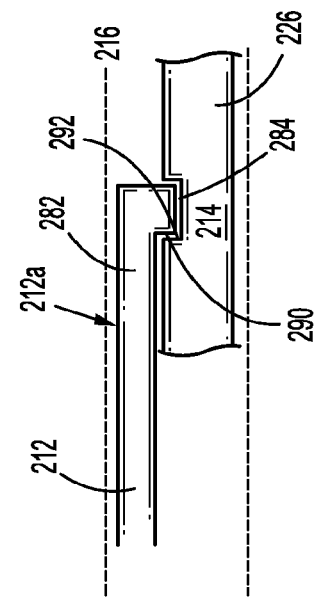
FIG. 10C is a side plan view of the interlock structure of FIG. 10B shown interlocked.
Figure 10B:
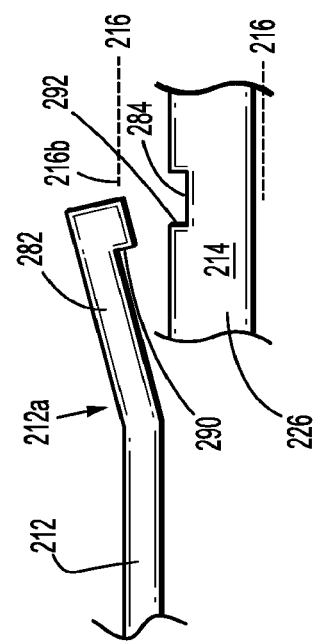
FIG. 10B is an enlarged side view of detail D of FIG. 10A.

FIGS. 10A-10C illustrate an embodiment of a stent 212 and inner tube 214 having another interlock configuration. Inner tube 214 has second interlock structures 284 in the form of slots including proximally facing interlock surfaces 292. The slots are sized to receive the first interlock structures 282 of the stent 212. The first interlock structures 282 are posts extending from the terminal ends of the stent 212 and include distally facing interlock surfaces 290. The first interlock structures 282 are fabricated from a shape memory or super alloy material that include a first position that is biased to extend radially outward from the longitudinal axis of the stent 212, as illustrated in FIG. 10B. The first interlock structures 282 are forced into a second position when the stent 212 is restrained in the compressed orientation by the sheath 216, as shown in FIG. 10C, to couple the first and second interlock structures 282, 284.

When the first and second interlock structures 282, 284 are coupled, the surfaces 290 and 292 engage each other to prevent distal movement of the stent 212 relative to the posts. As long as any portion of the sheath 216 overlies the first and second interlock structures 282, 284, the proximal end 212a of the stent 212 cannot expand and cannot axially move away from the second interlock structure 284. Accordingly, the stent 212 is not released from the stent attachment location 226 until a clinician has fully retracted the sheath 216 with the sheath distal end 216b retracted proximal to the proximal end of stent attachment location 226. Similar to the embodiments described above, it will be appreciated that the second interlock structures 284 may alternatively be provided in a collar (not shown) or retaining ring (not shown).

While the collar and/or retaining ring to which the second interlock structures may be attached is illustrated as a continuous structure encircling the inner tube, it will be appreciated that the collar and/or retaining ring may assume a variety of shapes. In embodiments, such as those shown in FIGS. 11A-11C, the collar 327 may define a gap 325 between free ends 321 and 323 (FIG. 11A), the free ends 321' and 323' of collar 327' may overlap (FIG. 11B), or the collar 327" may include two or more separate ring sectors 327a" and 327b" (FIG. 11C). While FIGS. 11A-11C illustrate embodiments of a collar having a discontinuous structure that may be positioned about the inner tube, it will be understood that the same or similar structure may be provided in a retaining ring.

The collar and/or retaining ring may be unattached to the inner tube such that the retaining ring may float, longitudinally move, or otherwise be displaceably arranged along the inner tube. FIG. 12A illustrates an embodiment of the second interlock structure 494 of an inner tube 414 positioned in a floating retaining ring 489. Floating retaining ring 489 includes interlock structure complementary to the interlock structure 82 of a stent 12 (e.g., FIG. 2A). It will be appreciated that any of the interlock structures described above may be providing on a floating retaining ring 489. Likewise, it will be appreciated that the discontinuous collar/retaining ring configurations described above may also be displaceably arranged about the inner tube.

FIG. 12B illustrates an embodiment of a floating retaining ring 489' having another floating configuration. Floating retaining ring 489' is attached at an end of an intermediate tube 419' disposed between the inner tube 414' and the sheath of the stent delivery system. The floating retaining ring 489' is free to move with intermediate tube 419' along inner tube 414'.

FIG. 12C illustrate another embodiment of a floating retaining ring 489" that is unattached to the inner tube 414', but attached to collar 427" by a flexible or elastic structure, such as spring 491', that allows the floating retaining ring 489" to move between a compressed state in which the floating retaining ring 489' abuts the collar 427" and a stretched state extending a predetermined distance from the collar 427' for limited movement of the floating retaining ring 489" along the inner tube 414".

Referring again to FIG. 5, splines 18 are radially projecting and extend at least partially along the length of the inner tubular member 14. In embodiments, splines 18 extend substantially the entire axial length of the inner tubular member 14. The radial dimension and axial length of each of the splines 18 is identical and, in embodiments, all splines 18 have a continuous uninterrupted length. However, it will be appreciated that the radial dimensions need not be identical and the splines 18 need not have an uninterrupted length. Instead, the splines 18 are an example of an embodiment of a spacer member used to maintain a spacing between the outer tubular member 16 and inner tubular member 14.

The spacer member 18 keeps the inner tubular member 14 in concentric alignment with the outer tubular member 16. This permits the use of a very small diameter inner tubular member 14 relative to the diameter of the outer tubular member 16 to increase the volume of the first lumen 40. This reduces any impediment to flow of contrast media through the first lumen 40 and increases the volume of contrast media within the first lumen. By reason of the splines 18, the inner tubular member 14 cannot bend relative to the outer tubular member 16, and since the splines 18 contact the outer tubular member 16 only at small surface areas along the length, very small friction results from sliding motion between the inner and outer tubular members 14, 16.

Figure 5:
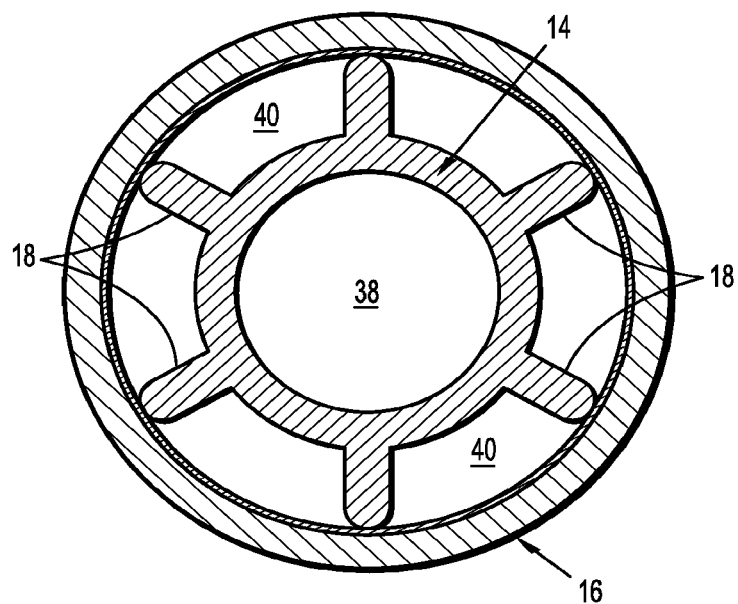
FIG. 5 is a cross-sectional view of the inner and outer tubular members of the stent delivery system of FIG. 1 taken along section line 5-5 of FIG. 3.
Figure 13B:
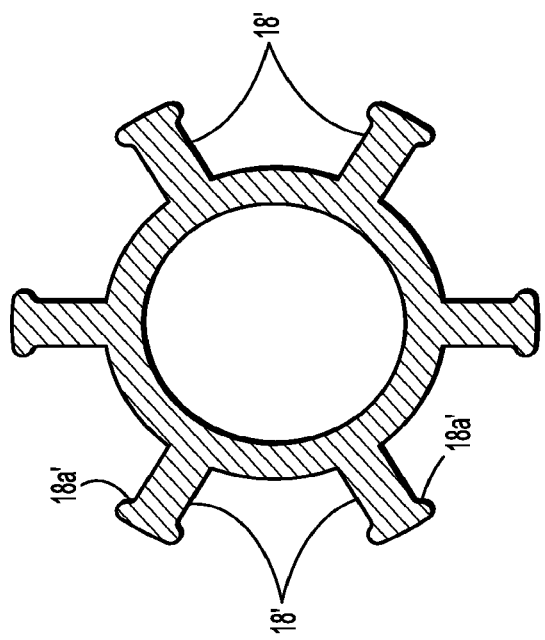
FIG. 13B is a cross-sectional view of an interlock structure of the inner tube in accordance with another embodiment of the present disclosure.
Figure 13A:
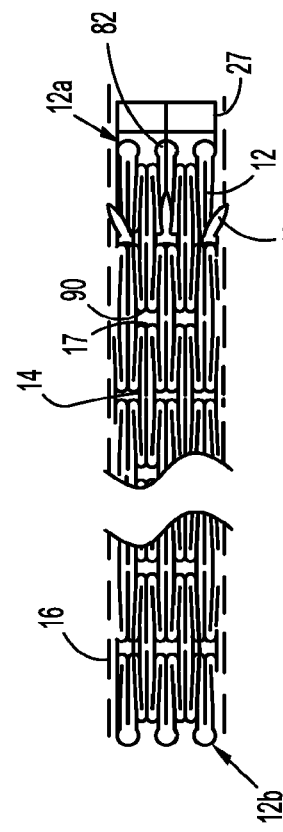
FIG. 13A is a cross-sectional view of a stent having an interlock structure interlocked with an interlock structure of an inner tube in accordance with an embodiment of the present disclosure.

With reference now to FIG. 13A, in conjunction with FIG. 5, splines 18 are may be provided on the stent attachment location 26 of the inner tube 14, in embodiments, distal to the proximal radiopaque marker 27. In some embodiments, the splines 18 are adjacent to the proximal radiopaque marker 27 or bonded thereto. Splines 18 are dimensioned to be received within cells 17 of stent 12 such that the splines 18 form the second interlocking structure of inner tube 14 and the cells 17 form the first interlocking structures of the stent 12. Splines 18 define axially facing interlock surfaces (not shown) that face in a proximal direction and cells 17 define axially facing interlock surfaces 90 that face in a distal direction. When the splines 18 and cells 17 are interlocked, the interlocks prevent the stent 12 from being axially withdrawn from the splines 18. Upon expansion of the stent 12, the cells 17 disengage the splines 18 thereby allowing the inner tube 14 of the catheter to be moved axially relative to the stent 12.

FIG. 13B illustrates an embodiment of the splines 18' including notches 18a' formed in the proximal end of the splines 18' to further prevent radial expansion and thus, axial movement of the stent 12 until the stent 12 has been fully unsheathed by the outer tube 16.

Figure 14B:
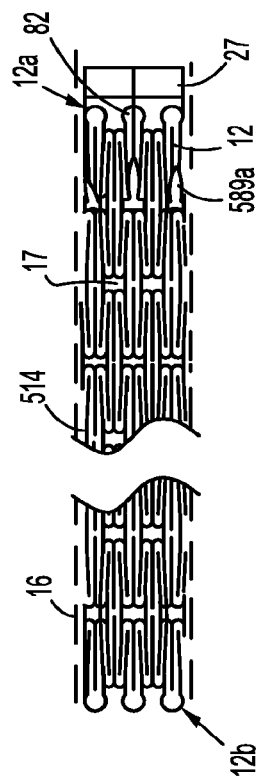
FIG. 14B is a cross-sectional view of a stent having an interlock structure interlocked with the interlock structure of FIG. 14A.
Figure 14A:
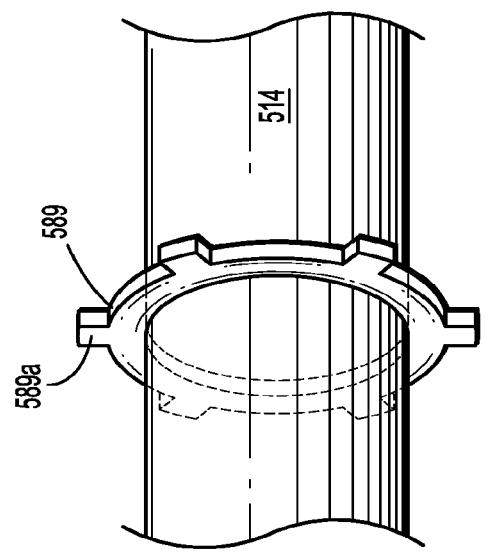
FIG. 14A is a perspective view of an interlock structure of an inner tube in accordance with an embodiment of the present disclosure.

FIGS. 14A and 14B illustrate an embodiment of an inner tube 514 having another interlock configuration. Retaining ring 589 is positioned on inner tube 514 and includes projections 589a extending radially outward from the inner tube 514. Retaining ring 589 is formed of a soft plastic, rubber, or other materials with elastomeric properties that may be temporary deform upon the application of pressure thereto. As illustrated in FIG. 14B, retaining ring 589 is positioned on the inner tube 514 with projections 589a extending through cells 17 of the stent 12 such that the projections 589a form the second interlocking structure of inner tube 14 and the cells 17 form the first interlocking structures of the stent 12. Projections 589a bend and overlie the stent 12 upon compression by sheath 16. When the sheath 16 is retracted to expose stent 12, the cells 17 of the stent 12 are released from the projections 589a of the retaining ring 589.

FIGS. 15A and 15B illustrate another embodiment of a deformable retaining ring 689. Retaining ring 689 is illustrated as a disk disposed about the inner tube 14. Retaining ring 689 is formed from a compressible material such as foam or an elastomer such as a soft urethane gel, silicone gel, thermoplastic elastomer, and the like. The diameter of the compressible retaining ring 689 is larger than the diameter of the outer tube 16. When the outer tube 16 is positioned over the stent 612, retaining ring 689 is deformed such that the outer radial edge 689a overlies and is pressed into the proximal end 612a of the stent 612, as illustrated in FIG. 15A. When the outer tube 16 is retracted the outer radial edge 689a of the retaining ring 689 follows the direction of the sheath to unveil the proximal end 612a of the stent 612 so that the stent 612 can expand, as illustrated in FIG. 15B.

FIG. 16A illustrate an embodiment of an inner tube having an interlock structure. Inner tube 714 may be formed or coated with a compressible material 714a such as a foam or elastomer radially extending from an outer surface thereof such that compressible material 714a of the inner tube 714 forms the interlock structure for retaining a stent 712. The compressible nature of the inner tube 714 allows the stent 712 to be positioned over and pressed into the inner tube 714 when sheathed by the outer tube 716 thereby preventing axial movement and release of the stent 712. When the outer tube 716 is retracted, the stent 712 expands and the cells 717 disengage the compressible material 714a.

FIG. 16B illustrates another embodiment of an inner tube 714' including fibers 714a extending radially therefrom. Fibers 714a may be straight or hooked fibers in a systematic or random configuration. Stent 712 may be compressed over the fibers 714a' of the inner tube 714' such that the cells 717 capture fibers 714a therebetween to prevent axial movement and release of the stent 712 until the outer tube 716 is retracted. Because the stent 712 will be retained throughout its entire length, the deployment would be more consistent with less of a chance of elongation or compression.

While the various embodiments of the present invention have related to stents and stent delivery systems, the scope of the present disclosure is not so limited. For example, while particularly suited for stent delivery systems, it will be appreciated that the various aspects of the present invention are also applicable to systems for delivering other types of self-expandable implants. By way of non-limiting example, other types of self-expanding implants include anastomosis devices, blood filters, grafts, vena cava filters, percutaneous valves, or other devices. Also, while the interlocks of the present disclosure are described, in embodiments, to be within 5 millimeters of an end of their corresponding implant to enhance deployment control, larger spacings could be used for certain applications.

Persons skilled in the art will understand that the devices and methods specifically described herein and illustrated in the accompanying figures are non-limiting exemplary embodiments, and that the description, disclosure, and figures should be construed merely exemplary of particular embodiments. It is to be understood, therefore, that the present disclosure is not limited to the precise embodiments described, and that various other changes and modifications may be effected by one skilled in the art without departing from the scope or spirit of the disclosure. Additionally, it is envisioned that the elements and features illustrated or described in connection with one exemplary embodiment may be combined with the elements and features of another without departing from the scope of the present disclosure, and that such modifications and variations are also intended to be included within the scope of the present disclosure. Accordingly, the subject matter of the present disclosure is not to be limited by what has been particularly shown and described, modifications and equivalents of the disclosed concepts are intended to be included within the scope of the claims.

What is claimed is:

1. A stent delivery system comprising:
an expandable stent comprising a first interlock structure;
an elongated inner member defining a longitudinal axis;
a floating retaining ring disposed on the elongated inner member and comprising a second interlock structure configured to engage the first interlock structure of the expandable stent, the floating retaining ring configured to move longitudinally relative to the elongated inner member; and
a sheath mounted on the elongated inner member, the sheath configured to be retracted with respect to the expandable stent to at least partially expose the expandable stent from the sheath.

2. The stent delivery system of claim 1, wherein the floating retaining ring is configured to be freely moveable along a longitudinal length of the elongated inner member.

3. The stent delivery system of claim 1, wherein the floating retaining ring is configured to be moveable over a predetermined longitudinal length of the elongated inner member.

4. The stent delivery system of claim 1, wherein the floating retaining ring is a discontinuous ring defining free ends at each respective end of the discontinuous ring.

5. The stent delivery system of claim 4, wherein the free ends of the floating retaining ring define a gap therebetween.

6. The stent delivery system of claim 4, wherein the free ends of the floating retaining ring at least partially overlap.

7. The stent delivery system of claim 4, wherein the floating retaining ring comprises separate ring sectors.

8. The stent delivery system of claim 1, wherein the second interlock structure is attached to an intermediate tube disposed between the elongated inner member and the sheath.

9. The stent delivery system of claim 1, wherein the second interlock structure is attached to the elongated inner member by a flexible structure that allows the second interlock structure to move a predetermined distance along the elongated inner member.

10. The stent delivery system of claim 9, wherein the flexible structure comprises a spring.

11. The stent delivery system of claim 1, wherein the expandable stent comprises a self-expanding stent.

12. The stent delivery system of claim 1, wherein the expandable stent comprises a balloon expandable stent.

13. A stent delivery system, which comprises:
an elongated inner member defining a longitudinal axis;
an expandable stent mounted about the elongated inner member;
a generally annular retainer mounted to the elongated inner member and dimensioned to releasably couple with the expandable stent, the generally annular retainer dimensioned for longitudinal movement along the elongated inner member; and
a sheath mounted on the elongated inner member, the sheath configured to be retracted with respect to the expandable stent to at least partially expose the expandable stent from the sheath.

14. The stent delivery system of claim 13, wherein the generally annular retainer and the stent comprise cooperating interlocking elements dimensioned to releasably couple the expandable stent to the generally annular retainer.

15. The stent delivery system of claim 13, wherein the stent is configured to be self-expanding, wherein, responsive to retraction of the sheath to a deployed position, the expandable stent is configured to expand and enable release of the stent from the retainer.

16. The stent delivery system of claim 13, wherein the generally annular retainer is a discontinuous ring defining free ends at each respective end of the discontinuous ring.

17. The stent delivery system of claim 16, wherein the free ends of the discontinuous ring define a gap therebetween.

18. The stent delivery system of claim 16, wherein the free ends of the discontinuous ring at least partially overlap.

19. The stent delivery system of claim 16, wherein the discontinuous ring comprises separate ring sectors.

20. The stent delivery system of claim 16, wherein the expandable stent comprises a self-expanding stent.

* * * * *